United States Patent [19]

Griengl et al.

[11] Patent Number: 5,346,816
[45] Date of Patent: Sep. 13, 1994

[54] ENZYMATIC PROCESS FOR THE ENANTIOSELECTIVE PREPARATION OF OPTICALLY ACTIVE CYANOHYDRINS

[75] Inventors: Herfried Griengl; Norbert Klempier, both of Graz; Peter Pöchlauer, Linz, all of Austria

[73] Assignee: Chemie Linz Gesellschaft m.b.H., Austria

[21] Appl. No.: 943,376

[22] Filed: Sep. 1, 1992

[30] Foreign Application Priority Data

Oct. 31, 1991 [AT] Austria ................. 2174/91

[51] Int. Cl.⁵ ................. C12P 13/00; C12P 41/00
[52] U.S. Cl. .................... 435/128; 435/280
[58] Field of Search ................. 435/128, 280

[56] References Cited

U.S. PATENT DOCUMENTS

| 4,859,784 | 8/1989 | Effenberger et al. | 549/491 |
| 5,008,192 | 4/1991 | Neidermeyer et al. | 435/128 |
| 5,122,462 | 6/1992 | Miethe et al. | 435/128 |

FOREIGN PATENT DOCUMENTS

| 615318 | 1/1990 | Australia . |
| 3823866 | 7/1988 | Fed. Rep. of Germany . |
| 4008412 | 7/1991 | Fed. Rep. of Germany . |

OTHER PUBLICATIONS

Smitskamp-Wilms et al., Recl. Trav. Chim. Pays-Bas 110(05): 209–15 (1991).
Kobayashi et al., *Chemistry Letters*, 931–934 The Chemistry Society of Japan (1986).
Ognyanov et al., *J. Am. Chem. Soc.*, 113(18) 6992–6996 (1991).
Selmar et al., *Physiologia Plantarum*, 75, 97–101 (1989).
Selmar et al., *Analytical Biochemistry*, 166, 208–211 (1987).
Westley et al., *The Journal of Organic Chemistry*, 33(10) 3978–3980 (1968).
Schurig et al., *Angewandte Chemie*, 102, 969–986 (1990).
*Chemical Abstracts*, 111, Ref: 132610u (1989).

Primary Examiner—Douglas W. Robinson
Assistant Examiner—S. Saucier
Attorney, Agent, or Firm—Wenderoth, Lind & Ponack

[57] ABSTRACT

Enantioselective process for the preparation of the S enantiomer of an optically active cyanohydrin by reacting an aldehyde or an asymmetric ketone with a cyanide group donor in the presence of an S-hydroxynitrile lyase in a diluent and isolating the cyanohydrin formed from the reaction mixture.

8 Claims, No Drawings

ENZYMATIC PROCESS FOR THE ENANTIOSELECTIVE PREPARATION OF OPTICALLY ACTIVE CYANOHYDRINS

The invention relates to an enzymatic process for the enantioselective preparation of optically active cyanohydrins from an aldehyde or asymmetric ketone and a cyanide group donor under the action of a hydroxynitrile lyase.

Cyanohydrins are important for example for the synthesis of alpha-hydroxy acids which are used for obtaining biologically active substances, for example pharmaceutical active substances, vitamins or else pyrethroid compounds.

A cyanohydrin can be prepared, for example, by an addition reaction of a cyanide group with the carbonyl carbon of an aldehyde or ketone, which results in enantiomer mixtures of optically active cyanohydrins if an aldehyde or an asymmetric ketone are employed. Since, in a biologically active enantiomer mixture, generally only one of the two enantiomers has biological activity, there has been no lack of attempts to find a process which allows a desired enantiomer of an optically active cyanohydrin to be prepared in as high an optical purity as possible.

For example, Chemistry Letters, The Chemical Society of Japan (1986), 931–934 discloses a process for the cyanohydrination of an aldehyde using a cyanide group donor and a synthetic dipeptide as catalyst. However, the enantioselectivity of this reaction is only moderate, and the optical purity of the products is unsatisfactory.

It is known from U.S. Pat. No. 5,008,192 that aliphatic, aromatic or heteroaromatic aldehydes or ketones can be reacted with hydrocyanic acid in the presence of an oxynitrilase, during which process corresponding R- or S-cyanohydrins are formed enantioselectively. However, the handling of hydrocyanic acid causes problems since its boiling point is low. Moreover, hydrocyanic acid is very poisonous and its use in an industrial scale process is therefore avoided as much as possible.

J. Am. Chem. Soc. 1991, 113, 6992–6996 describes a process for the preparation of R-cyanohydrins by reacting aromatic or aliphatic aldehydes with acetone cyanohydrin in the presence of a D-oxynitrilase. To obtain products which are enriched in enantiomers, the process must be carried out in the presence of an organic solvent which is not miscible with water, since an aqueous solution only results in racemization of the product.

Surprisingly, an enantioselective process for the preparation of the S enantiomer of an optically active cyanohydrin has been found in which the products are obtained in high optical purity and in which the use of hydrocyanic acid and an organic solvent can be dispensed with. S-Cyanohydrins which are derived from aliphatic aldehydes can thus be prepared for the first time with the aid of an S-hydroxynitrile lyase.

Accordingly, the invention relates to an enantioselective process for the preparation of the S enantiomer of an optically active cyanohydrin by reacting an aldehyde or an asymmetric ketone with a cyanide group donor, which process is characterized in that the aldehyde or the ketone is reacted with the cyanide group donor in a diluent in the presence of an S-hydroxynitrile lyase, whereupon the cyanohydrin formed is isolated from the reaction mixture.

The starting materials employed in the process according to the invention are an aldehyde or an asymmetric ketone, a cyanide group donor, a hydroxynitrile lyase and a diluent.

Aldehydes in this context are to be understood as meaning aliphatic, aromatic or heteroaromatic aldehydes. Asymmetric ketones are aliphatic, aromatic or heteroaromatic ketones in which the carbonyl carbon atom is substituted by different substituents. Substances which are preferably reacted are aldehydes, particularly preferably aliphatic or aromatic aldehydes. Such aldehydes and ketones are known or can be prepared in the customary manner.

Suitable cyanide group donors are a cyanohydrin of the general formula $R_1R_2C(OH)(CN)$ in which $R_1$ and $R_1$ independently of one another denote hydrogen or a hydrocarbon group which is unsubstituted or substituted with groups which are inert under the reaction conditions, or $R_1$ and $R_2$ together denote an alkylene group having 4 or 5 C atoms, where $R_1$ and $R_2$ are not simultaneously hydrogen. The hydrocarbon groups are aliphatic or aromatic, preferably aliphatic, groups. $R_1$ and $R_2$ preferably denote alkyl groups having 1 to 6 C atoms, and acetone cyanohydrin is particularly preferred as cyanide group donor.

The cyanide group donor can be prepared by known processes. Cyanohydrins, in particular acetone cyanohydrin, are also commercially available.

Suitable hydroxynitrile lyases are S-hydroxynitrile lyases, for example from *Sorghum bicolor* and *Hevea brasiliensis*. The hydroxynitrile lyase from *Hevea brasiliensis* has proved to be particularly suitable. The hydroxynitrile lyase can be employed in purified or unpurified form, and either as such or immobilized. The hydroxynitrile lyase can be prepared and purified, for example, by precipitation with ammonium sulfate followed by gel filtration, such as described by D. Selmar et al., Physiologia Plantarum 75 (1989), 97–101.

The reaction is carried out in a diluent. It has proved particularly advantageous that the reaction can be carried out the reaction in an aqueous diluent without an addition of organic solvents which rapidly inhibit the activity of the enzyme, which, unexpectedly, results in no racemization of the product. However, the reaction according to the invention can also be carried out in an organic diluent or in the presence of an organic solvent. In this process, the organic solvent can act as a co-solvent in an aqueous system or as a solvent in a two-phase system, for example in a membrane reactor. Organic diluents which can be used are aliphatic or aromatic hydrocarbons which are optionally halogenated, alcohols, ethers or esters. Organic co-solvents which can be employed are organic solvents which are miscible with water, such as alcohols, and solvents which can be employed in a two-phase system are organic solvents which are not miscible with water such as, for example, aliphatic or aromatic hydrocarbons which are optionally halogenated, ethers or esters. The reaction is preferably carried out not in the presence of an organic solvent but in an aqueous diluent. The aqueous diluent employed is water, an aqueous salt solution or an aqueous buffer solution. An aqueous buffer solution is preferably used, particularly preferably an aqueous buffer solution comprising sodium citrate. The pH in this process should be below 7, preferably approximately 3 to 5.

Approximately 150 to 300 g of diluent and 500 to 2000 IU activity of hydroxynitrile lyase, preferably approximately 800 to 1500 IU, are added per g of aldehyde or asymmetric ketone. One IU (International Unit) stands for the formation of one micromole of product per minute and per gram of crude enzyme isolation. The required quantity of the hydroxynitrile lyase in question is best determined in an activity test, for example as described by Selmar et al., Analytical Biochemistry 166 (1987), 208–211.

At least one mole, preferably 1 to 2 moles, of cyanide group donor are added per mole of aldehyde or keto group employed.

The reaction mixture is shaken or stirred at temperatures from approximately 0° C. up to the deactivation temperature of the hydroxynitrile lyase, preferably from 20° to 30° C. During this process, the cyanide group is transferred from the cyanide group donor to the carbonyl carbon atom of the aldehyde or ketone employed, and the resulting product is mostly the S enantiomer of the optically active cyanohydrin corresponding to the aldehyde or ketone employed. The progress of the reaction is monitored by gas chromatography.

When the reaction has ended, the cyanohydrin formed can be extracted from the reaction mixture with the aid of an organic solvent which is not miscible with water, such as aliphatic or aromatic, optionally halogenated hydrocarbons, for example pentane, hexane, benzene, toluene, methylene chloride, chloroform, chlorobenzenes, ethers such as diethyl ether or diisopropyl ether, or esters, such as ethyl acetate, or mixtures of such solvents. If the product extracted is not sufficiently pure, this can be followed by a purification step. The purification can be carried out by a known method, and best results are obtained with chromatography.

In a preferred embodiment, approximately 100 mg of aldehyde in 15 to 30 g of an aqueous buffer solution having a pH of approximately 4 and comprising sodium citrate is shaken at room temperature with 2 moles of acetone cyanohydrin per mole of aldehyde or keto group employed and 200 IU activity of hydroxynitrile lyase from *Hevea* brasiliensis. The progress of the reaction is monitored by gas chromatography. When the reaction has ended, the reaction mixture is extracted with methylene chloride, and the organic phase is dried and evaporated. The residue can be purified further by column chromatography.

The process according to the invention produces optically active S-enriched cyanohydrins in a simple manner and dispenses with the use of hydrocyanic acid and an organic solvent. The process is therefore an enrichment of the art.

EXAMPLE 1

100 mg of caproic aldehyde (1 mmol) were dissolved in 20 ml of 0.1 molar citrate buffer having a pH of 4, the solution was treated with 1 g of crude enzyme isolation having an activity of 100 IU per gram in the form of a lyophilized powder obtained as described by D. Selmar et al., Physiologica Plantarum 75 (1989), 97 to 101, and with 168 mg of acetone cyanohydrin (2 mmol), and the mixture was shaken for 2 hours in a shaker at room temperature. The reaction was monitored by gas chromatography. When the reaction had ended, the mixture was extracted three times using 25 ml of methylene chloride in each case. The organic phases were combined and dried over sodium sulfate, and the solvent was evaporated on a Rotavapor.

This gave 114 mg, that is 90% of theory, of S-caproic aldehyde cyanohydrin of an enantiomeric purity ee of 84%.

EXAMPLE 2

80 mg of benzaldehyde (0.75 mmol) and 128 mg of acetone cyanohydrin (1.5 mmol) were reacted with 1 g of the crude enzyme isolation described in Example 1 in 15 ml of 0.1 molar citrate buffer (pH=4), as described in Example 1.

This gave 45 mg, that is 45% of theory, of S-benzaldehyde cyanohydrin of an enantiomeric purity ee of 94%.

The optical purity of the aldehyde cyanohydrins formed was determined as menthyl carbonate by means of gas chromatography on a capillary column as described by J. W. Westley et al., J. Org. Chem. 33 (1968), 3978–3980.

The optical purity of the ketone cyanohydrins was determined by gas chromatography using a chiral separating phase as described by V. Schurig et al., Ang. Chemie 102 (1990), 969–986.

We claim:

1. An enantioselective process for the preparation of the S-enantiomer of an optically active cyanohydrin which comprises reacting an aldehyde or an asymmetric ketone with a cyanohydrin of the formula $R_1R_2C(OH)(CN)$ in which $R_1$ and $R_2$ independently of one another denote hydrogen or a hydrocarbon group which is unsubstituted or substituted with groups which are inert under the reactions conditions or $R_1$ and $R_2$ together denote an alkylene group having 4 or 5 C-atoms, where $R_1$ and $R_2$ are not simultaneously hydrogen, in a diluent in the presence of an S-hydroxynitrile lyase of the genus *Hevea* or *Sorghum* and isolating cyanohydrin formed, from the reaction mixture.

2. The process according to claim wherein said aldehyde is an aliphatic, aromatic or heteroaromatic aldehyde.

3. The process according to claim 1, comprising reacting an aliphatic or aromatic aldehyde.

4. The process according to claim 1, comprising employing a cyanohydrin of the formula $(R_1)(R_2)C(OH)(CN)$ in which $R_1$ and $R_2$ denote alkyl groups as the cyanide group donor.

5. The process according to claim 1, comprising employing acetone cyanohydrin as the cyanide group donor.

6. The process according to claim 1, comprising employing an aqueous diluent.

7. The process according to claim 1, comprising carrying out the reaction in an aqueous buffer solution at a pH of 3 to 5.

8. The process according to claim 1, comprising extracting the cyanohydrin formed from the reaction mixture and purifying it by chromatography.

* * * * *